US005769783A

United States Patent [19]

Fowler

[11] Patent Number: 5,769,783

[45] Date of Patent: Jun. 23, 1998

[54] SURGICAL RETRACTOR STAY APPARATUS

[75] Inventor: James M. Fowler, Houston, Tex.

[73] Assignee: Lone Star Medical Products, Inc., Houston, Tex.

[21] Appl. No.: 671,405

[22] Filed: Jun. 27, 1996

[51] Int. Cl.[6] ....................................................... A61B 11/02
[52] U.S. Cl. ............................................ 600/226; 600/227
[58] Field of Search ..................................... 600/201, 226, 600/227, 231, 233, 229; 24/300, 265 EE, 265 H

[56] References Cited

U.S. PATENT DOCUMENTS

| | | |
|---|---|---|
| 170,573 | 11/1875 | Lesh ........................................ 24/300 X |
| 334,711 | 1/1886 | Lorenz ............................ 24/265 EE X |
| 3,515,129 | 6/1970 | Truhan . |
| 3,762,401 | 10/1973 | Tupper . |
| 3,916,879 | 11/1975 | Cotten ................................. 600/227 X |
| 4,185,636 | 1/1980 | Gabbay et al. . |
| 4,254,763 | 3/1981 | McCready et al. . |
| 4,257,406 | 3/1981 | Schenk . |
| 4,263,900 | 4/1981 | Nicholson . |
| 4,274,398 | 6/1981 | Scott, Jr. . |
| 4,321,916 | 3/1982 | McKee . |
| 4,337,762 | 7/1982 | Gauthier . |
| 4,337,763 | 7/1982 | Petrassevich . |
| 4,344,420 | 8/1982 | Forder . |
| 4,355,631 | 10/1982 | LeVahn . |
| 4,380,999 | 4/1983 | Healy . |
| 4,387,706 | 6/1983 | Glass . |
| 4,412,532 | 11/1983 | Anthony . |
| 4,421,107 | 12/1983 | Estes et al. . |
| 4,421,108 | 12/1983 | Cabrera et al. . |
| 4,430,991 | 2/1984 | Darnell . |
| 4,434,791 | 3/1984 | Darnell . |
| 4,559,677 | 12/1985 | Tracy ........................................ 24/300 |

FOREIGN PATENT DOCUMENTS

| | | |
|---|---|---|
| 1222141 | 2/1971 | United Kingdom . |
| 1550254 | 8/1979 | United Kingdom . |
| 1550255 | 8/1979 | United Kingdom . |

OTHER PUBLICATIONS

Bone Retractors and Retractors AESCULAP©, Product catalog p. 319 (No Date).
*Thermoplastic Replaces Metal in Disposable Abdominal Retractor*, MD&M Review, ULTOP® Conveyor Modules (No Date).
I.S.I. North America, Inc. *International Surgical Instruments* Brochure (No Date).
Accurate Surgical & Scientific Instruments Corporation Brochure (No Date).

*Primary Examiner*—Jeffrey A. Smith
*Attorney, Agent, or Firm*—Pravel, Hewitt, Kimball & Krieger

[57] ABSTRACT

A surgical stay apparatus provides a frame that can be annular and conforming to a patient's body at a surgical site. An opening allows a surgeon to access the surgical site through the central portion of the frame. A stay includes a handle body having proximal and distal ends. The first bore extends through the handle body communicating at least with the proximal end of the handle body. The second bore extends at least a partial distance through the handle body and communicates with the proximal surface of the body. An elastic member extends through the first bore, the elastic member having an elongated portion that extends from the distal end of the handle body and a short proximal end that is positioned at the handle body occupying at least a portion of the first bore. A hook member having proximal and distal end portions occupies the second bore of the handle body, the hook member has a curved hook at the distal end portion of the handle body for retracting body tissue. The handle body can be of an injection molded plastic construction. The elastic member can be an elongated section of hollow silicone tubing. The hook can be shaped to snap into one of the bore of the handle body for anchoring the hook to the handle body. In one embodiment, a plastic injection molded stay handle can have a "V" slot to retain the distal end of the elastic tubing.

19 Claims, 5 Drawing Sheets

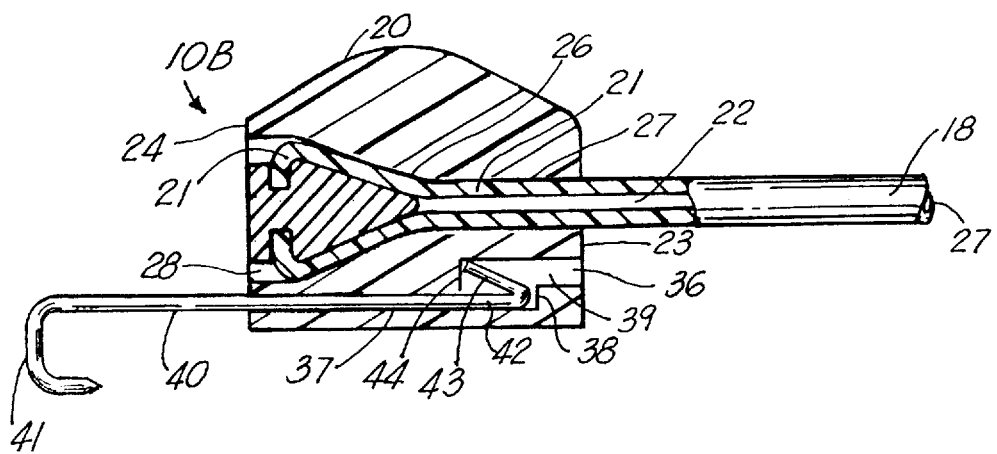
FIG. 3
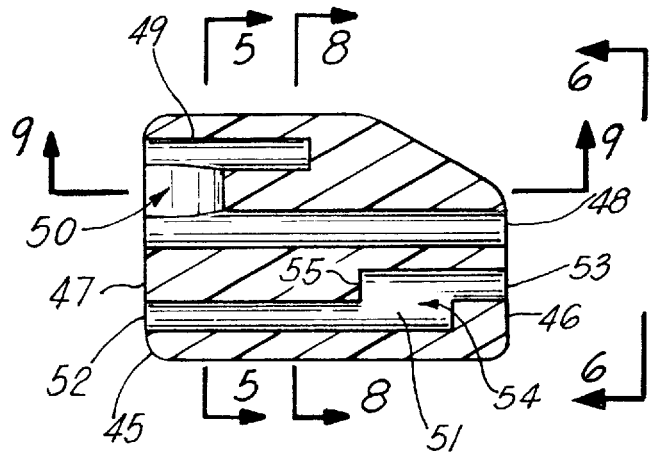
FIG. 4
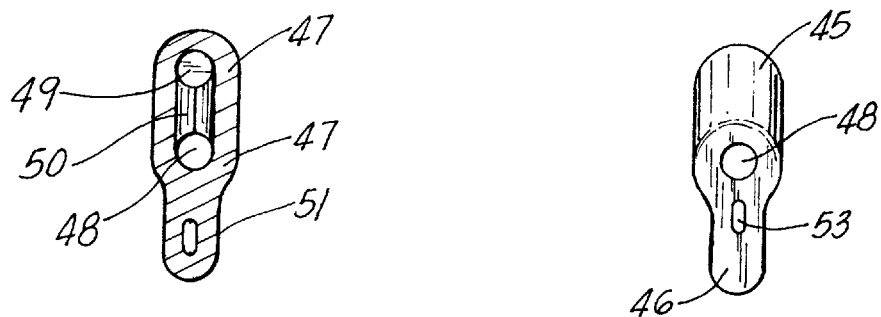
FIG. 5
FIG. 6

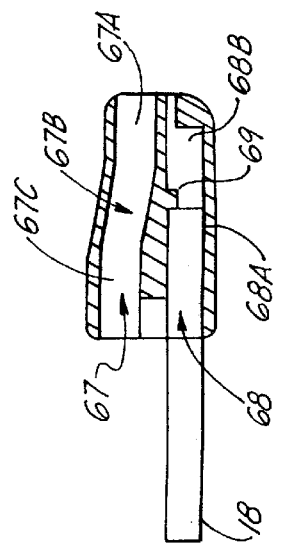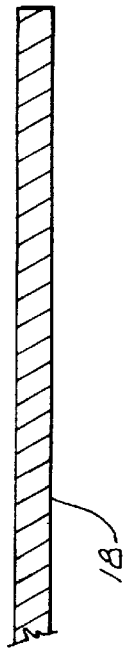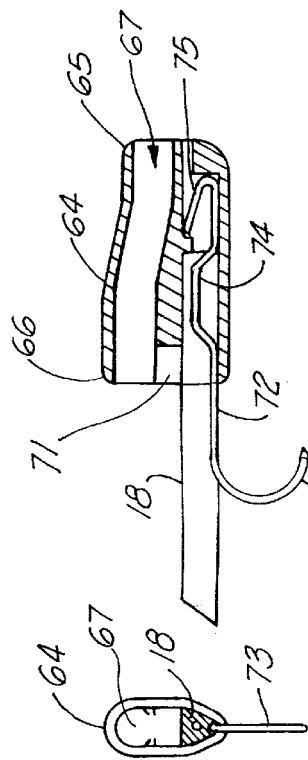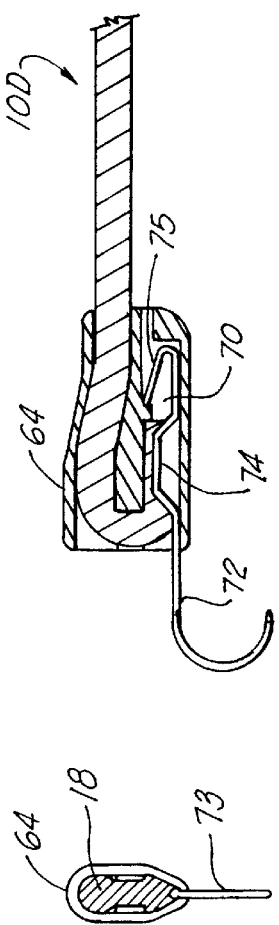

5,769,783

SURGICAL RETRACTOR STAY APPARATUS

SPECIFICATION

BACKGROUND OF THE INVENTION

1. Field of the Invention

The present invention relates to surgical retractors and surgical retractor stays. More particularly, the present invention relates to an improved elastic surgical retractor stay and includes a handle body having separate bore sections that respectively accept an end portion of an elastic member and a hook member for engaging the tissue, wherein the handle body has connecting portions that allow separate spaced apart connections to be made between the elastic member and the handle body as well as between the hook and the handle body.

2. Description of the Related Art

During the course of a surgical procedure or operation, the surgeon opens the patient with a scalpel, forming an incision and surgical site. As the surgeon cuts deeper, the operating room staff typically holds tissue away from the operative field using retractors.

Most retractors are one piece metallic implements that retract a wound in a non-yielding manner. Manipulation and movement of the surgeon as well as movement caused by contracting muscles or tissues of the patient can result in bruising or tearing of tissue.

Once an incision is separated and retracted, there is often a need for multiple stays in the form of sutures for holding various tissues, for example different organs. Elastic surgical retractor systems are in commercial use that include elastic stays, each having an elongated elastic member that is typically a hollow length of elastic tubing. The elastic tubing provides proximal and distal end portions. The distal end portion carries an elongated hook constructed of wire.

The wire hook has a proximal end that is placed in the distal end of the bore of the hollow tubing. A shrink wrap is placed over the hook and tubing to hold the proximal end of the wire hook firmly in position within the bore of the tubing at the distal end. The embedded portion of the wire hook member is usually recurved or folded. This folded proximal portion of the wire hook expands the tubing slightly, forming a vertically extended portion that defines a handle.

Various patents have issued for elastic stay retractor systems. A surgical retractor array system is disclosed in U.S. Pat. No. 4,434,791, issued to W. Dale Darnell on Mar. 6, 1984. This surgical retractor system comprises an array of standardized, interchangeable, annular retractor frame sections of various shapes of which the end portions are configured to permit the interchangeable, hinged connection of the various shaped frames in forming generally annular retractor units adaptable to conform to fit the surface contours of various patients upon which a surgical operation is to be performed. This retractor frame is designed to accept yielding rubber or like elastic stays.

Other recent patents have issued that relate to elastic type retractor stays and related retractor frames and systems.

U.S. Pat. No. 4,274,398, issued to Frank B. Scott, Jr., issued Jun. 23, 1981, discloses a surgical retractor which includes an annular frame conformed to fit the surface contour of the portion of the body to be operated on. At least one stay includes an elastic member and a tissue holding hook. The frame has a plurality of notches spaced about its periphery. The elastic portion of the stay is in the form of a length of hollow elastic tubing adapted to be inserted into one of the notches of the frame and held in place by friction to retract the tissue. The hook is a single, curved wire member. It has a folded proximal end that fits the hollow bore of the elastic tube.

U.S. Pat. No. 4,430,991, issued to W. Dale Darnell, issued on Feb. 14, 1984, discloses a surgical retractor stay with a single tissue holding hook affixed to the elastic hollow tubing member of the stay by a retaining member. The retaining member has a body in which the hook shank is embedded with the sharp end of the hook extending from one end of the body. A stud with a tapered knob on its outer end extends outwardly from the other end of the retaining member body. The size and configuration of the knob and stud enable them to be tightly retained within an end portion of the hollow tubing that is stretchingly installed thereover. A surgical tube connector for joining a pair of hollow elastic surgical tube members having an elongated stud with tapered knobs at each end in which the stud and knobs are dimensioned for tight fitting containment within the end portions of the hollow tube members stretchingly installed thereover.

SUMMARY OF THE INVENTION

The present invention provides an improved surgical stay apparatus that can be connected to a frame placed upon the patient's body at a surgical site. The frame can provide a plurality of notches that receive an end portion of an elastic member. In one embodiment, a handle body provides proximal and distal ends, a first bore that extends through the handle body communicating at least with the proximal end of the handle body, the first bore provides a central longitudinal axis.

In the first embodiment, a second bore extends at least a partial distance through the handle body and communicates with the proximal surface of the body. The elastic member extends through the first bore of the handle body. The elastic member has an elongated portion that extends away from the distal end of the handle body and a short proximal end portion that is positioned at the handle body by occupying at least a portion of the first bore.

A retracting hook has proximal and distal end portions. The proximal end portion occupies the second bore of the handle body. The hook member has a curved hook at its distal end of the handle body for engaging tissue during retraction.

In the first embodiment, the first bore has a linear central longitudinal axis. A plug forms a connection with an end portion of the elastic member at one of the bores in the first embodiment (see FIG. 2A). In a second embodiment, the proximal end of the hook engages an offset that forms an anchor within the second bore. In a third embodiment, the first bore includes two separate sections that are generally parallel to one another (see FIG. 4). The elastic member folds at a notch positioned in between the two bore sections of the first bore.

A fourth embodiment provides a handle body that includes two bore sections. One of the bore section is a longitudinal bore that extends between the proximal and distal sections of the body. The second bore is sized and shaped to receive both the hook portion of the retractor and the extreme distal end of the elastic member. To assemble the third embodiment, the user routes the distal end of the elastic member through the first bore, then folds the distal end and places the extreme distal portion into the second bore. The user then anchors the extreme distal end of the elastic member to the second bore by inserting the hook into the second bore.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 2A is a partial, sectional, elevational view of the preferred embodiment of the apparatus of the present invention illustrating the handle body, hook, and elastic member portions;

FIG. 3 is a fragmentary, sectional, elevational view of the second embodiment of the apparatus of the present invention;

FIG. 4 is a partial sectional elevation view of a third embodiment of the apparatus of the present invention;

FIG. 5 is a sectional view taken along lines 5—5 of FIG. 4;

FIG. 6 is a sectional view taken along lines 6—6 of FIG. 4;

FIG. 11 is a side sectional view of the fourth embodiment of the apparatus of the present invention;

FIG. 12 is an end view of the fourth embodiment of the apparatus of the present invention;

FIG. 13 is a partial sectional elevational view of the fourth embodiment of the apparatus of the present invention;

FIG. 14 is another partial sectional elevational view of the fourth embodiment of the apparatus of the present invention; and FIG. 15 is a partial end view of the fourth embodiment of the apparatus of the present invention.

DETAILED DESCRIPTION OF THE PREFERRED EMBODIMENT

Figure 1:
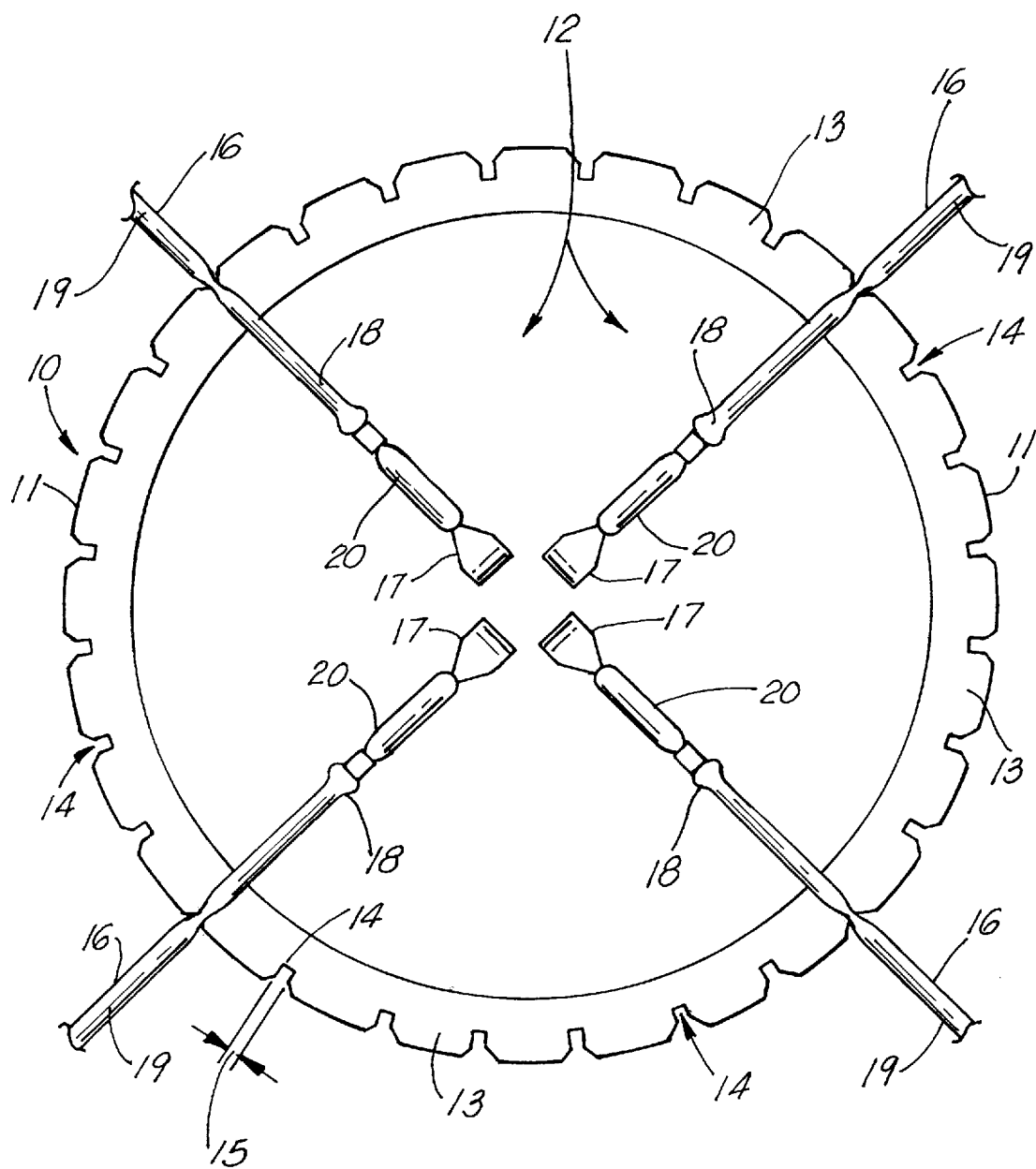
FIG. 1 is a plan top view of the preferred embodiment of the apparatus of the present invention.

Turning now to the drawings, FIG. 1 shows generally the preferred embodiment of the apparatus of the present invention designated generally by the numeral 10. In FIG. 1, retractor apparatus 10 includes a frame 11 having an open center 12. The frame 11 can have a circular or annular shape as shown. This allows an open center 12 to be placed in conformity with the surface of the patient's body and about a surgical site. Frame 11 has an annular flange 13 with a plurality of notches 14. Each notch 14 has a width 15.

A plurality of retractor stays 16 can be placed about frame 11 as shown in FIG. 1. Each stay 16 includes an elongated elastic member 18. Elastic member 18 is preferably a length of either hollow elastic tubing or solid elastic material that fits a notch 14 at the proximal 19 end of the length of elastic member 18. The diameter of each length of elastic tubing 18 is preferably thicker than the width 15 of each notch 14.

Each retractor stay 16 includes a proximal end 19 that forms a connection with handle 20. Handle 20 carries at its distal end a hook 17 that is used to engage tissue to be retracted. Hook 17 can be of uniform diameter wire construction (preferably stainless steel or like surgical metallic material).

Figure 2:
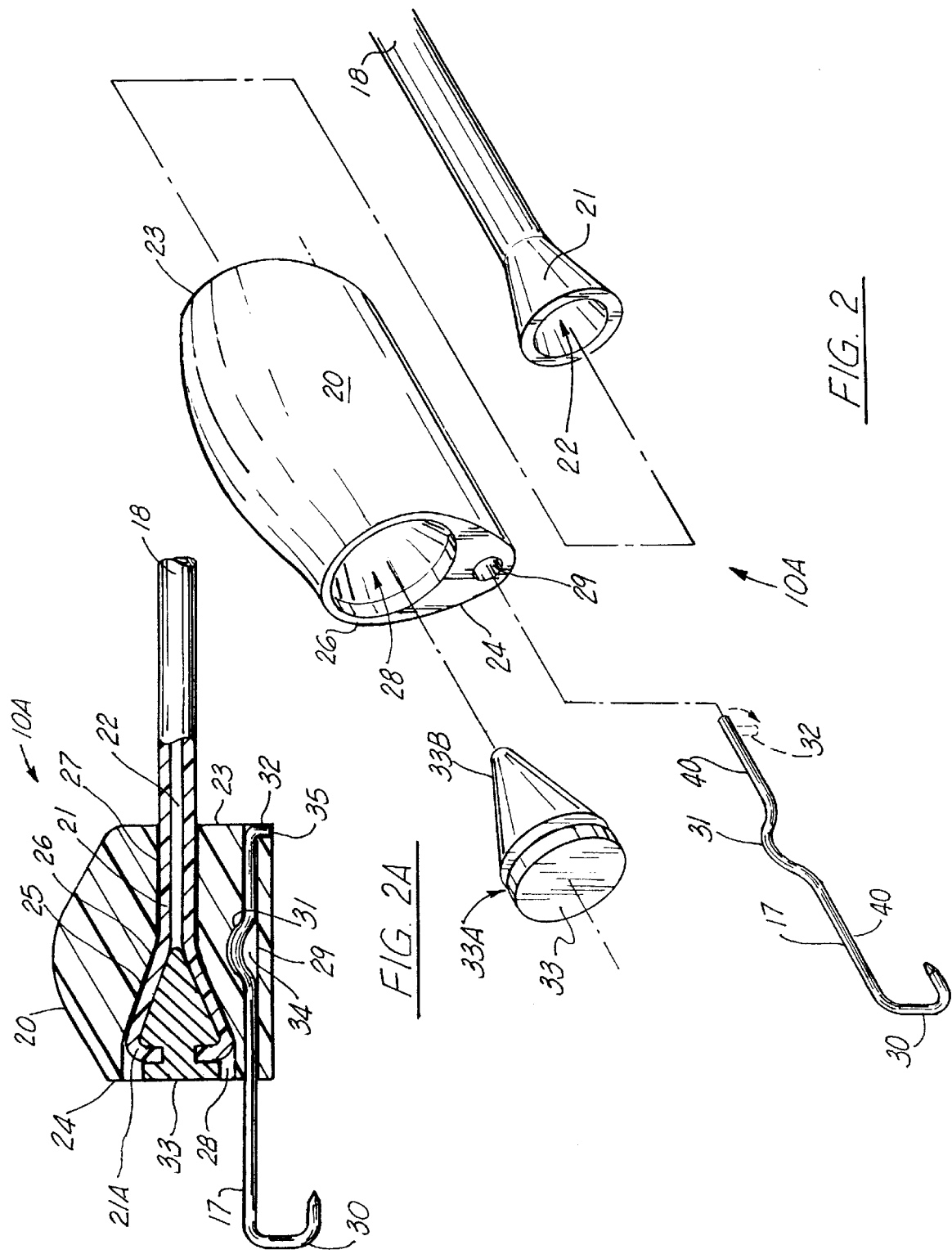
FIG. 2 is a exploded, perspective view of the handle body portion of the preferred embodiment of the apparatus of the present invention.

In FIGS. 2, 2A and 3, a first embodiment of the retractor stay is shown, designated as 10A in FIGS. 2 and 2A. In FIGS. 2 and 2A, handle body 20 has distal end 24 and proximal end 23. A first hollow bore 25 is provided through handle body 20, communicating with proximal end 23 and distal end 24. In FIG. 2A, elastic member 18 is preferably an elongated length of hollow elastic tubing having a wall 21 and a full length central longitudinal open ended bore 22 that communicates with the end portions of the elastic member 18.

First bore 25 has a smaller bore section 26 that is generally cylindrically shaped and preferably of a uniform diameter. A larger section 27 of first bore 25 is conically shaped, bounded by a conical wall 28. The large section 27 of first bore 25 is largest at distal 24 end of handle body 20.

A second bore 29 extends through handle body 20, communicating with both proximal end 23 and distal end 24. The second bore 29 carries a hook member 17. Hook member 17 has a distal curved end 30, a middle section that includes a curved, off-set 31, and a pair of cylindrically shaped linear sections 40. A transversely extending proximal end 32 defines an anchor that cooperates with a transverse section 35 of second bore 29. Bore 29 corresponds generally to the shape of the middle and proximal ends of hook 17. Second bore 29 has an enlarged section 34 that receives the curved offset 31 of hook 17.

Plug 33 fits enlarged section 27 of first bore 25 as shown in FIG. 2A. Plug 33 is preferably tapered, having a conical section 33B that corresponds in shape to the conical wall 28 of large bore section 27 of first bore 25. Annular grove 33A can receive the extreme distal end of elastic member 18 as shown in FIG. 2A.

In order to assemble the elastic member 18 to handle body 20 and plug 33, the elastic member 18 is first channelled through first bore 25 beginning at proximal end 23. The extreme distal end 21A of elastic member 18 is then positioned at the distal end 24 of handle body 20. Tapered conical portion 33B of plug 33 fits inside bore 22 of elastic member 18 at the distal 21A end thereof. The conical portion 33B of plug 33 dilates elastic member 18 at distal end 24 so that the plug 33 and distal end 21A of elastic member 18 fit enlarged section 27 of first bore 25 as shown in FIG. 2A.

In FIG. 3, an alternate construction (second embodiment) of retractor stay is shown, designated as 10B. In FIG. 3, handle body 20 is similarly constructed to the embodiment of FIGS. 2 and 2A. In FIG. 3, retractor stay 10B has a hook 40 with a curved distal end 41 that fits bore 36. Bore 36 is comprised of a pair of off-set bore sections, including cylindrical distal section 37 and cylindrical proximal section 39. Transverse section 38 of bore 36 provides a flat surface 44 that receives hook proximal end 42 at its anchor 43 as shown in FIG. 3. The hook 40 has a predominant linear portion that extends between the distal hook end 41 and the anchor 43, as shown in FIG. 3.

Figure 7:
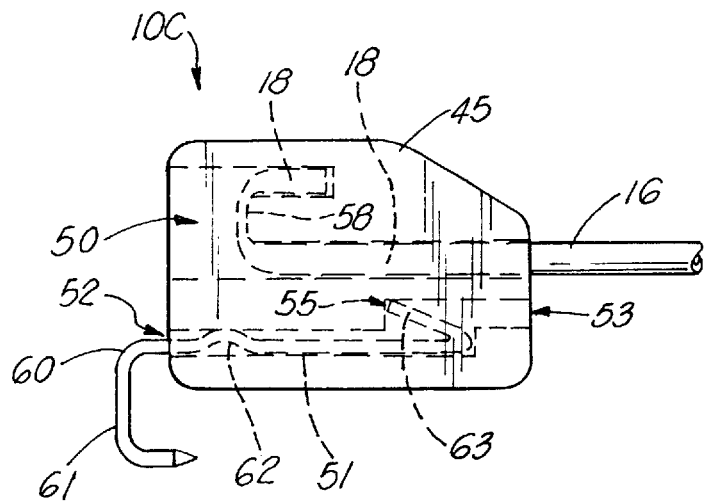
FIG. 7 is a partial elevational view of the third embodiment of the apparatus of the present invention.
Figure 9:
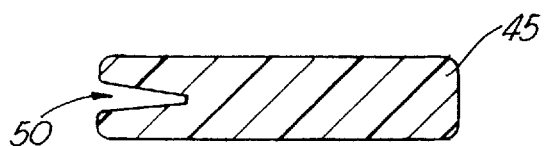
FIG. 9 is a sectional view taken along lines 9—9 of FIG. 4.
Figure 8:
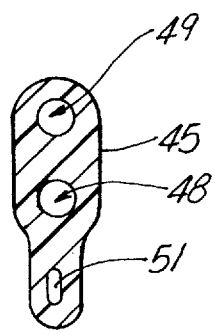
FIG. 8 is a sectional view taken along lines 8—8 of FIG. 4.

FIGS. 4–10 show a third embodiment of the retractor stay, designated as l0C in FIG. 7. In the embodiment of FIGS. 4–10, handle body 45 has a proximal end 46 and a distal end 47. A first bore section 48 is cylindrically shaped, extending completely through the handle body 45 and communicating with proximal 46 and distal 47 ends of body 45 as shown in FIG. 4. First bore section 48 is generally cylindrically shaped. Second bore section 49 is also cylindrically shaped, but only extends about half way through the handle body 45 as shown in FIG. 4. Bore section 49 begins at distal end 47 of handle body 45 and terminates about half the distance between the proximal 46 and distal 47 ends of handle body 45. Notch 50 extends between the bore sections 48 and 49.

A third bore 51 is a bore that has off-set sections. Bore 51 has a cylindrically shaped distal section 52, a cylindrically shaped proximal section 53, and a transverse section 54 that connects the distal 52 and proximal 53 sections. The cylindrically shaped sections 52 and 53 are off-set, having parallel central longitudinal axes.

Figure 10:
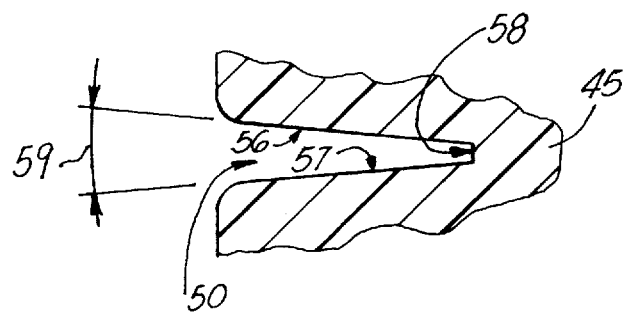
FIG. 10 is an enlarged fragmentary sectional view of the notch portion of the handle body of the third embodiment of the apparatus of the present invention.

Stop 55 is defined by an inner end portion of the cylindrical bore section 53 as shown in FIG. 4. Notch 50 is defined by a pair of flat surfaces 56, 57 as shown in FIG. 10. The surfaces 56, 57 are flat surfaces that form an acute angle 59. A stop 58 defines the inner end portion of notch 50 as shown in FIG. 10. Hook 60 attaches to handle body 45 at bore 51. The hook 60 has a distal hook end portion 61, a curved off-set 62, and a proximal anchor portion 63 as shown in FIG. 7. During use, the user forces the proximal 63 end of hook 60 into the cylindrical bore section 52 until the anchor 63 registers at flat surface 55.

FIGS. 11–15 show a fourth embodiment of the apparatus of the present invention designated generally by the numeral 10D in FIG. 11. FIGS. 13 and 14 show handle body 64 having proximal end 65 and distal end 66. A first bore 67 extends between proximal end 65 and distal end 66. The first bore 67 has three bore sections 67A, 67B, and 67C that form angles with each other as shown in FIG. 13. The first bore 67 receives elastic tubing member 18 as shown in FIG. 11. Second bore 68 has a first cylindrical section 68A and a second cylindrically shaped section 68B. A stop 69 extends laterally to define a narrowed diameter section 70 in between bore sections 68A and 68B as shown in FIGS. 11 and 13. A notch 71 is provided at distal 66 end of body 64, the notch being V-shaped to grasp elastic member 18 as shown in FIGS. 11 and 12 upon complete assembly.

The second bore 68 receives hook member 72. The hook member 72 includes a curved portion 73, and offset 74 and a folded anchor 75 as shown in FIGS. 11 and 14.

In order to assemble the embodiment of FIG. 11, the user first inserts the extreme distal end of elastic member 18 into cylindrical sections 68A of bore 68 as shown in FIG. 13. The user ten routes the proximal end of elastic member 18 through the bore 67 beginning at the distal 66 end of body 64. The user then anchors the distal end of hook 72 at anchor 75 into the second bore 68 as shown in FIG. 11 so that the offset 74 clamps the distal end of elastic member 18 as shown in FIG. 11. The notch 71 also grips elastic tubing 18. The user then pulls on the proximal end of elastic member 18 until the elastic member 18 is fully engaged at notch 71 as shown in FIG. 11.

The following table lists the parts numbers and parts descriptions as used herein and in the drawings attached hereto.

PARTS LIST

| Part Number | Description |
| --- | --- |
| 10 | retractor apparatus |
| 10A | retractor stay |
| 10B | retractor stay |
| 10C | retractor stay |
| 10D | retractor stay |
| 11 | frame |
| 12 | open center |
| 13 | annular flange |
| 14 | notch |
| 15 | width of notch |
| 16 | elastic retractor stay |
| 17 | hook |
| 18 | elastic member |
| 19 | proximal end |
| 20 | handle body |
| 21 | tubing wall |
| 21A | tubing end |
| 22 | hollow bore |
| 23 | proximal end |
| 24 | distal end |
| 25 | first bore |
| 26 | smaller section |
| 27 | larger section |
| 28 | conical wall |
| 29 | second bore |
| 30 | distal end |
| 31 | curved section |
| 32 | proximal end |
| 33 | plug |
| 34 | enlarged section |
| 35 | transverse section |
| 36 | bore |
| 37 | cylindrical distal section |
| 38 | transverse section |
| 39 | cylindrical proximal section |
| 40 | linear section |
| 41 | hook distal end |
| 42 | proximal end |
| 43 | anchor |
| 44 | flat surface |
| 45 | handle body |
| 46 | proximal end |
| 47 | distal end |
| 48 | first bore section |
| 49 | second bore section |
| 50 | notch |
| 51 | bore |
| 52 | cylindrical section |
| 53 | cylindrical section |
| 54 | transverse section |
| 55 | flat surface |
| 56 | flat surface |
| 57 | flat surface |
| 58 | flat surface |
| 59 | angle |
| 60 | hook |
| 61 | distal end |
| 62 | bend |
| 63 | anchor |
| 64 | handle body |
| 65 | proximal end |
| 66 | distal end |
| 67 | first bore |
| 67A | section |
| 67B | section |
| 67C | section |
| 68 | second bore |
| 69 | stop |
| 70 | narrowed section |
| 71 | notch |
| 72 | hook |
| 73 | curved distal end |
| 74 | offset |
| 75 | anchor |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgical retractor stay apparatus comprising:
   a) frame that conforms to a patient's body at a surgical site;
   b) a stay connectable to the frame that includes a handle body having proximal and distal ends;
   c) a first bore with a central longitudinal axis that extends through the handle body, communicating with at least the proximal end of the handle body;
   d) a second bore that extends at least a partial distance through the handle body and communicating with the proximal end of the body;
   e) an elastic member that extends through the first bore, the elastic member having an elongated portion that extends from the distal end of the handle body and a short proximal end that is positioned at the handle body occupying at least a portion of the first bore;
   f) a hook member having proximal and distal end portions, the proximal end portion occupying the second bore of the handle body; and
   g) the hook member having a curved hook at the distal end portion of the handle body.

2. The surgical retractor stay of claim 1, wherein the first bore has a linear central longitudinal axis.

3. The surgical retractor stay of claim 1, wherein the first bore has a central longitudinal axis that includes two sections that offset with respect to one another.

4. The surgical retractor stay of claim 1, wherein the first bore includes two sections that are generally parallel to one another.

5. The surgical retractor stay of claim 1, wherein the first bore has a smaller diameter section and a larger section that is larger in diameter than the smaller diameter section.

6. The surgical retractor stay of claim 1 further comprising a locking member that forms a connection with the first bore and a portion of the elastic member, said locking member locking the elastic member to the handle body at the first bore.

7. The surgical retractor stay of claim 1 further comprising a locking plug inserted into the handle body at an open end portion of the first bore for anchoring the elastic member to the handle body.

8. The surgical retractor stay of claim 1, wherein the first bore has a proximal end portion that communicates with the proximal end of the handle body and a distal end portion.

9. The surgical retractor stay of claim 8 further comprising a locking plug inserted into the handle body at the distal end portion of the first bore.

10. The surgical retractor stay of claim 8 further comprising a tapered locking plug inserted into the handle body at the distal end of the first bore, the elastic member being hollow and the plug having a pointed end that is shaped to fit into and expand the distal end of the elastic member.

11. The surgical retractor stay of claim 8, wherein the first bore has a distal tapered section and further comprising a locking plug that can be inserted into the handle body at the tapered section of the first bore, wherein the first bore has a maximum diameter at the distal end of the hand body.

12. The surgical retractor stay of claim 1, wherein the elastic member is hollow along at least a portion of its length.

13. The surgical retractor stay of claim 12 further comprising a locking plug inserted into the handle body at an open end portion of the first bore for anchoring the elastic member to the handle body.

14. The surgical retractor stay of claim 13, wherein the plug occupies a portion of the elastic member bore.

15. The surgical retractor stay of claim 12, wherein the first bore has a proximal end portion that communicates with the proximal end of the handle body and a distal end portion.

16. The surgical retractor stay of claim 15 further comprising a locking plug inserted into the handle body at the distal end portion of the first bore.

17. The surgical retractor stay of claim 1, wherein the second bore comprises multiple bore sections having axes that are generally parallel.

18. The surgical retractor stay of claim 1, wherein the second bore comprises multiple bore sections having axes that are angularly oriented relative to one another.

19. The surgical retractor stay of claim 1, wherein the hook member curved hook portion extends away from the handle body, positioned to grip selected patient tissue and further comprising a hook anchor and a shoulder on the handle body that receives the hook anchor for transferring load between the hook member and handle body.

\* \* \* \* \*